(12) United States Patent
Rousu et al.

(10) Patent No.: US 11,701,166 B2
(45) Date of Patent: Jul. 18, 2023

(54) CATHETER TIPS AND RELATED METHODS (71) Applicant: Biosense Webster (Israel) Ltd., Yokneam (IL)

(72) Inventors: Corey Rousu, Irwindale, CA (US); Daniele Ghidoli, Irwindale, CA (US); Matthew Hitzeroth, Irwindale, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 299 days.

(21) Appl. No.: 17/097,400

(22) Filed: Nov. 13, 2020

(65) Prior Publication Data
US 2021/0177490 A1 Jun. 17, 2021

Related U.S. Application Data (60) Provisional application No. 62/949,332, filed on Dec. 17, 2019.

(51) Int. Cl.
*A61B 18/14* (2006.01)
*C25D 7/04* (2006.01)
(Continued)

(52) U.S. Cl.
CPC .............. *A61B 18/14* (2013.01); *C25D 3/48* (2013.01); *C25D 3/50* (2013.01); *C25D 5/56* (2013.01); *C25D 7/04* (2013.01); *A61B 2018/00077* (2013.01); *A61B 2018/00613* (2013.01); *A61B 2018/1405* (2013.01); *A61B 2218/002* (2013.01)

(58) Field of Classification Search
CPC .......... A61B 18/14; A61B 2018/00077; A61B 2018/00613; A61B 2018/1405; A61B 2218/002; C25D 3/48; C25D 3/50; C23D 5/56; C23D 7/04
See application file for complete search history.

(56) References Cited

U.S. PATENT DOCUMENTS

| 5,462,648 A * | 10/1995 | Wakabayashi | B41J 2/1631 205/75 |
| 5,762,637 A * | 6/1998 | Berg | A61M 25/001 604/523 |
| 6,916,409 B1 * | 7/2005 | Callol | C25F 7/00 204/297.05 |

FOREIGN PATENT DOCUMENTS

| WO | 2017146465 A1 | 8/2017 | |
| WO | WO-2017146465 A1 * | 8/2017 | ............ A61M 25/00 |

OTHER PUBLICATIONS

International Search Report & Written Opinion dated Apr. 1, 2021, from corresponding International Application No. PCT/US2020/070907.

* cited by examiner

*Primary Examiner* — Linda C Dvorak
*Assistant Examiner* — Abigail Bock
(74) *Attorney, Agent, or Firm* — Troutman Pepper Hamilton Sanders LLP (57) ABSTRACT

A method of manufacturing a catheter tip by electroplating a conductive material over an insert comprising a negative to a domelike shape thereby forming a shape of the catheter tip comprising a dome with the domelike shape, selectively positioning a plurality of irrigation holes between outer and inner surfaces of the catheter tip, removing the insert thereby leaving the catheter tip and the plurality of irrigation holes, and electropolishing the catheter tip. In other examples, the insert is not removed and instead the step of electroplating causes the insert to be encapsulated with the conductive material thereby forming the catheter tip.

20 Claims, 8 Drawing Sheets

SIMULTANEOUSLY PERFORMING ANY METHOD PREVIOUSLY DESCRIBED TO MANUFACTURE THE PLURALITY OF CATHETER TIPS ―810

(51) Int. Cl.
*C25D 5/56* (2006.01)
*C25D 3/48* (2006.01)
*C25D 3/50* (2006.01)
*A61B 18/00* (2006.01)

┌─────────────────────────────────────────────────────┐
│ ELECTROPLATING A CONDUCTIVE MATERIAL OVER A         │
│ PLURALITY OF INSERTS COMPRISING A NEGATIVE TO A     │ 710
│ DOMELIKE SHAPE THEREBY FORMING A PLURALITY OF       │
│ CATHETER TIPS INCLUDING THE DOMELIKE SHAPE, THE     │
│ STEP OF ELECTROPLATING CAUSING THE INSERTS TO BE    │
│ ENCAPSULATED WITH THE CONDUCTIVE MATERIAL           │
│ THEREBY FORMING THE CATHETER TIPS                   │
└─────────────────────────────────────────────────────┘

┌─────────────────────────────────────────────────────┐
│ SELECTIVELY POSITIONING A PLURALITY OF IRRIGATION   │
│ HOLES BETWEEN OUTER AND INNER SURFACES OF           │ 720
│ EACH RESPECTIVE CATHETER TIP                        │
└─────────────────────────────────────────────────────┘

┌─────────────────────────────────────────────────────┐
│ ELECTROPOLISHING EACH CATHETER TIP OF THE           │ 730
│ PLURALITY OF CATHETER TIPS                          │
└─────────────────────────────────────────────────────┘

SIMULTANEOUSLY PERFORMING ANY METHOD PREVIOUSLY DESCRIBED TO MANUFACTURE THE PLURALITY OF CATHETER TIPS — 810

Fig. 8

CATHETER TIPS AND RELATED METHODS

CROSS-REFERENCE TO RELATED APPLICATIONS

This application claims priority to U.S. provisional patent application No. 62/949,332 filed Dec. 17, 2019, the contents of which are incorporated herein by reference in their entirety as if set forth verbatim.

FIELD

The present disclosure relates generally to producing tips for use in ablation catheters, and particularly to methods for mass production of tips for use in ablation catheters.

BACKGROUND

Cardiac arrhythmias, such as atrial fibrillation, occur when regions of cardiac tissue abnormally conduct electric signals to adjacent tissue, thereby disrupting the normal cardiac cycle and causing asynchronous rhythm.

Procedures for treating arrhythmia include surgically disrupting the origin of the signals causing the arrhythmia, as well as disrupting the conducting pathway for such signals. By selectively ablating cardiac tissue by application of energy via a catheter, it is sometimes possible to block or modify the propagation of unwanted electrical signals from one portion of the heart to another. The ablation process destroys the unwanted electrical pathways by formation of non-conducting lesions.

Currently, radiofrequency (RF) ablation catheter tips each have to be individually machined to create irrigation holes and/or to create the shell. This is both time and labor intensive, which increases overall costs but also reduces repeatable and scalable manufacturing.

The solution of this disclosure resolves these and other problems of the art.

SUMMARY

Accordingly, the inventors of this disclosure have recognized that there is a need for manufacturing multiple catheter tips at once with one or more removable inserts or molds that can be electroplated to create a catheter tip including a dome. Many inserts could be processed at once depending on the size.

In some examples, a method of manufacturing a catheter tip is disclosed. The method includes electroplating a conductive material over an insert including a negative to a domelike shape thereby forming a shape of the catheter tip including a dome with the domelike shape, selectively positioning a plurality of irrigation holes between outer and inner surfaces of the catheter tip, removing the insert thereby leaving the catheter tip and the plurality of irrigation holes and electropolishing the catheter tip.

In some examples, the catheter tip being generally tubular with a dome-like cover.

In some examples, the insert is generally tubular with an inner lumen.

In some examples, the insert includes a plastic.

In some examples, the plastic includes Acrylonitrile Butadiene Styrene (ABS).

In some examples, the plastic includes Polycarbonate.

In some examples, the conductive material includes gold.

In some examples, the conductive material includes palladium.

In some examples, the conductive material includes platinum.

In some examples, the method includes forming the insert by molding a plastic material from a mold of a size and shape of the catheter tip.

In some examples, the step of selectively positioning the plurality of irrigation holes includes the steps of selecting an irrigation hole diameter, selecting a catheter tip wall thickness, determining a lateral and a vertical growth rate of the material, and determining a size of an insert irrigation hole negative based on the irrigation hole diameter, the wall thickness, and the lateral and the vertical growth rate of the material.

In some examples, the lateral and the vertical growth rate of the material is 1:1, and the step of determining a size of an insert irrigation hole negative includes adding the irrigation hole diameter with the catheter tip wall thickness.

In some examples, the step of selectively positioning the plurality of irrigation holes is done simultaneously.

In some examples, the step of electroplating the conductive material over the insert includes axially aligning a pin with a longitudinal axis of the insert, and holding, by the pin, the insert during electroplating.

In some examples, the step of selectively positioning the plurality of irrigation holes includes forming an irrigation hole pattern on the catheter tip out of a secondary non-plateable material.

In some examples, the secondary non-plateable material is nylon.

In some examples, the secondary non-plateable material is polypropylene.

In some examples, the secondary non-plateable material is polyester.

In some examples, the method includes setting an outer diameter of the insert to an inner diameter of the catheter tip.

In some examples, the method includes thickening a lower edge of the catheter tip with the secondary non-plateable material thereby preventing formation of a rounded edge adjacent a base of the catheter tip.

In some examples, the method includes positioning a step of the secondary non-plateable material at a lower edge adjacent a base of the catheter tip.

In some examples, the step includes a height of approximately 0.002" thereby thickening the lower edge and preventing formation of a rounded edge.

In some examples, the method includes offsetting a hole diameter of one or more holes in the hole pattern by a wall thickness.

In some examples, the step of selectively positioning the plurality of irrigation holes includes oversizing an operational catheter tip diameter by a wall thickness of the catheter tip.

In some examples, the step of selectively positioning the plurality of irrigation holes includes sizing a manufacture diameter of the irrigation holes by an operational catheter tip diameter plus a wall thickness of the catheter tip.

In some examples, the method includes maintaining, following the step of selectively positioning the plurality of irrigation holes and the step of removing the insert, a 1:1 ratio of lateral and vertical growth of the conductive material.

In some examples, the method includes overmolding the secondary non-plateable material onto the insert.

In some examples, holes of the hole pattern are configured for being filled by the secondary material.

In some examples, the step of removing the insert includes melting the insert thereby leaving leave behind the catheter tip.

In some examples, the step of removing the insert includes dissolving the insert in acid thereby leaving leave behind the catheter tip.

In some examples, the step of electropolishing the dome includes removing surface roughness and/or burrs.

In some examples, a method of manufacturing a plurality of catheter tips is disclosed. The method includes simultaneously performing a method of any preceding claim to manufacture the plurality of catheter tips.

In some examples, a catheter tip made by any method of this disclosure.

In some examples, a method of manufacturing a plurality of catheter tips is disclosed. The method includes electroplating a conductive material over a plurality of inserts including a negative to a domelike shape thereby forming a plurality of domes including the domelike shape, selectively positioning a plurality of irrigation holes between outer and inner surfaces of each respective dome, removing each respective insert thereby leaving a respective dome, and electropolishing domes of the plurality of catheter tips.

In some examples, the insert being generally tubular with an inner lumen.

In some examples, each respective insert includes a plastic.

In some examples, the plastic includes Acrylonitrile Butadiene Styrene (ABS).

In some examples, the plastic includes Polycarbonate.

In some examples, the conductive material includes gold.

In some examples, the conductive material includes palladium.

In some examples, the conductive material includes platinum.

In some examples, the method includes forming each respective insert by molding a plastic material from a mold of a size and shape of each respective catheter tip.

In some examples, the step of selectively positioning the plurality of irrigation holes includes the steps of selecting an irrigation hole diameter, selecting a catheter tip wall thickness, determining a lateral and a vertical growth rate of the material, and determining a size of an insert irrigation hole negative based on the irrigation hole diameter, the wall thickness, and the lateral and the vertical growth rate of the material.

In some examples, the lateral and the vertical growth rate of the material is 1:1, and the step of determining a size of an insert irrigation hole negative includes adding the irrigation hole diameter with the catheter tip wall thickness.

In some examples, the step of selectively positioning the plurality of irrigation holes is done simultaneously.

In some examples, the step of electroplating the conductive material over the plurality of inserts includes axially aligning a pin with a longitudinal axis of each respective insert, and holding, by the respective pin, the respective insert during electroplating.

In some examples, the step of selectively positioning the plurality of irrigation holes includes forming an irrigation hole pattern on each respective catheter tip out of a secondary non-plateable material.

In some examples, the secondary non-plateable material is nylon.

In some examples, the secondary non-plateable material is polypropylene.

In some examples, the secondary non-plateable material is polyester.

In some examples, the method includes setting an outer diameter of each respective insert to an inner diameter of the respective catheter tip.

In some examples, the method includes thickening a lower edge of each respective catheter tip with the secondary non-plateable material thereby preventing formation of a rounded edge adjacent a base of the respective catheter tip.

In some examples, the method includes positioning a step of the secondary non-plateable material at a lower edge adjacent a base of the respective catheter tip.

In some examples, the step includes a height of approximately 0.002" thereby thickening the lower edge and preventing formation of a rounded edge.

In some examples, the method includes offsetting a hole diameter of one or more holes in the hole pattern by a wall thickness.

In some examples, the step of selectively positioning the plurality of irrigation holes includes oversizing an operational catheter tip diameter by a wall thickness of each respective catheter tip.

In some examples, the step of selectively positioning the plurality of irrigation holes includes sizing a manufacture diameter of the irrigation holes by an operational catheter tip diameter plus a wall thickness of each respective catheter tip.

In some examples, the method includes maintaining, following the step of selectively positioning the plurality of irrigation holes and the step of removing the insert, a 1:1 ratio of lateral and vertical growth of the conductive material of each respective catheter tip.

In some examples, the method includes overmolding the secondary non-plateable material onto each respective insert.

In some examples, the holes of the hole pattern are configured for being filled by the secondary material.

In some examples, the step of removing each respective electroplated insert includes melting the respective insert thereby leaving leave behind the respective catheter tip.

In some examples, the step of removing each respective electroplated insert includes dissolving the respective insert in acid thereby leaving leave behind the respective catheter tip.

In some examples, the step of electropolishing the plurality of catheter tips includes removing surface roughness and/or burrs.

In some examples, a catheter tip is disclosed that is made by a process including the steps of electroplating a conductive material over an insert having a negative to a domelike shape thereby forming a catheter tip comprising a dome, selectively positioning a plurality of irrigation holes between outer and inner surfaces of the dome, removing the insert thereby leaving the catheter tip, and electropolishing the catheter tip.

In some examples, a plurality of catheter tips is disclosed that is made by a process including the steps of electroplating a conductive material over a plurality of inserts comprising a negative to a domelike shape thereby forming a plurality of catheter tips each having a dome, selectively positioning a plurality of irrigation holes between outer and inner surfaces of each respective catheter tip, removing each respective insert thereby leaving a respective catheter tip, and electropolishing each catheter tip of the plurality of catheter tips.

The present disclosure will be more fully understood from the following detailed description of embodiments thereof, taken together with the drawings.

BRIEF DESCRIPTION OF THE DRAWINGS

The above and further aspects of this disclosure are further discussed with reference to the following description in conjunction with the accompanying drawings, in which like numerals indicate like structural elements and features in various figures. The drawings are not necessarily to scale, emphasis instead being placed upon illustrating principles of the disclosure. The figures depict one or more implementations of the inventive devices, by way of example only, not by way of limitation.

DETAILED DESCRIPTION

The term "electroplating" in this disclosure is intended to mean the act of coating an object by electrolytic deposition with a metal, such as chromium, silver, gold, platinum, palladium, and the like.

As used herein, the term "non-plateable material" can mean any material that does not easily, or is incapable of, being electroplated. Such materials can include one or combination of nylon, polypropylene, polyester, non-blended plastics, the material marketed under Valox® which are thermoplastic polymer resins, and the like.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values±20% of the recited value, e.g. "about 90%" may refer to the range of values from 71% to 99%.

Medical devices such as some types of catheters include electrodes that are used, for example, for conducting electrical signals to or from patient tissue. Embodiments of the present disclosure that are described hereinbelow provide methods for producing a catheter tip for use with electrodes having low impedance at low frequencies. In principle, it is possible to produce such electrodes by coating (e.g., soldering or gluing) discrete locations of a catheter with conductive (e.g., metal) layers. These metal layers reduce the impedance of the electrode at low frequencies, but such coating processes are inefficient for high volume manufacturing (HVM). The disclosed techniques enable producing the catheter tips using very large-scale integration (VLSI) processes that enable high productivity in HVM. The disclosed techniques help to increase the functionality of catheter tips by producing them at HVM without compromising production costs. Furthermore, using VLSI processes on catheter tips reduce the production cost of the distal end.

Figure 1:
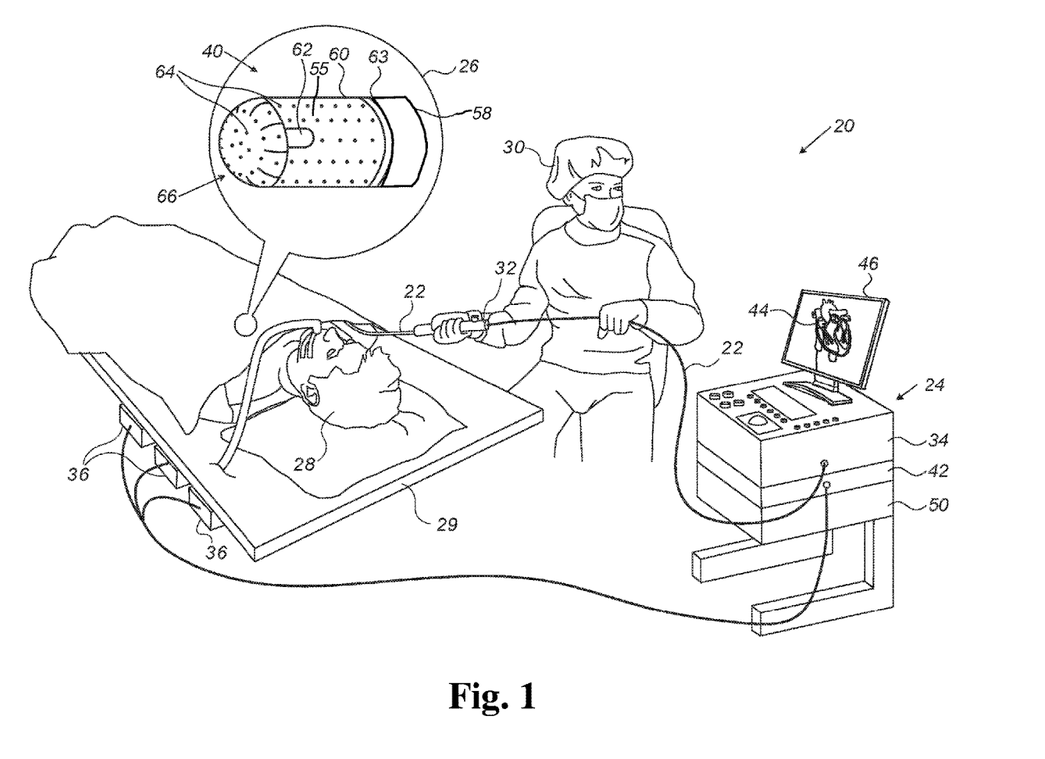
FIG. 1 is a schematic illustration of a system for ablating tissue of a subject, in accordance with some embodiments of the present disclosure.

FIG. 1 is a schematic, pictorial illustration of a catheterization system 20, in accordance with an embodiment of the present disclosure. System 20 includes a probe, in the present example a cardiac catheter 22, and a control console 24. Catheter 22 may be used for any suitable therapeutic and/or diagnostic purposes, such as sensing signals from a heart (not shown) of a patient 28.

Console 24 can include a processor 34, typically a general-purpose computer, with suitable front end and interface circuits for receiving signals from catheter 22 and for controlling the other components of system 20 described herein. Console 24 can include a driver circuit 42, which drives magnetic field generators 36 placed at known positions external to patient 28 lying on table 29, e.g., below the patient's torso.

In some embodiments, console 24 includes a memory 50 and a display 46, configured to display data, such as an image 44 of at least part of the heart of patient 28. In some embodiments, image 44 may be acquired using a computerized tomography (CT) system, by a magnetic resonance imaging (MRI) scanner, or using any other suitable anatomical imaging system. A physician 30 (such as an interventional cardiologist) inserts catheter 22 through the vascular system of patient 28 lying on a table 29. Catheter 22 includes a distal-end assembly 40, shown in an inset 26. Physician 30 moves assembly 40 in the vicinity of the target region in the heart by manipulating catheter 22 with a manipulator 32 near the proximal end of catheter 22. The proximal end of catheter 22 is connected to interface circuitry in processor 34.

Reference is now made to insert 26 with distal-end assembly 40, which can include a flexible printed circuit board (PCB) sheet 60 disposed around an internal member 69. In some embodiments, assembly 40 further includes a dome 66. Sheet 60 and/or dome 66 may be perforated so as to form one or more irrigation holes 64, which are configured to allow irrigation fluid to flow out from the insertion tube when irrigating the tissue of the heart, for example during an ablation procedure.

Assembly 40 once finished can include one or more electrodes 62 and/or one or more ring electrodes 63, which are configured to conduct electrical signals to or from the tissue of the heart. During a medical procedure, such as a cardiac mapping, electrodes 62 and/or ring electrodes 63 are brought into contact with the tissue of the heart, so as to sense electrical signals originated therefrom. Assembly 40 can be used for ablating tissue of the heart.

In some embodiments, processor 34 typically includes a general-purpose processor, which is programmed in software to carry out the functions described herein. The software may be downloaded to the computer in electronic form, over a network, for example, or it may, alternatively or additionally, be provided and/or stored on non-transitory tangible media, such as magnetic, optical, or electronic memory.

The configuration of assembly 40 shown in FIG. 1 is an example configuration, which is chosen purely for the sake of conceptual clarity. In alternative embodiments, any other suitable configuration can also be used. For example, the size and shape of assembly 40, and the number and locations of electrodes 62 and/or ring electrodes 63 may be implemented using any suitable components and layout appropriate for conducting a suitable medical procedure on tissue of any organ of patient 28.

Figure 2:
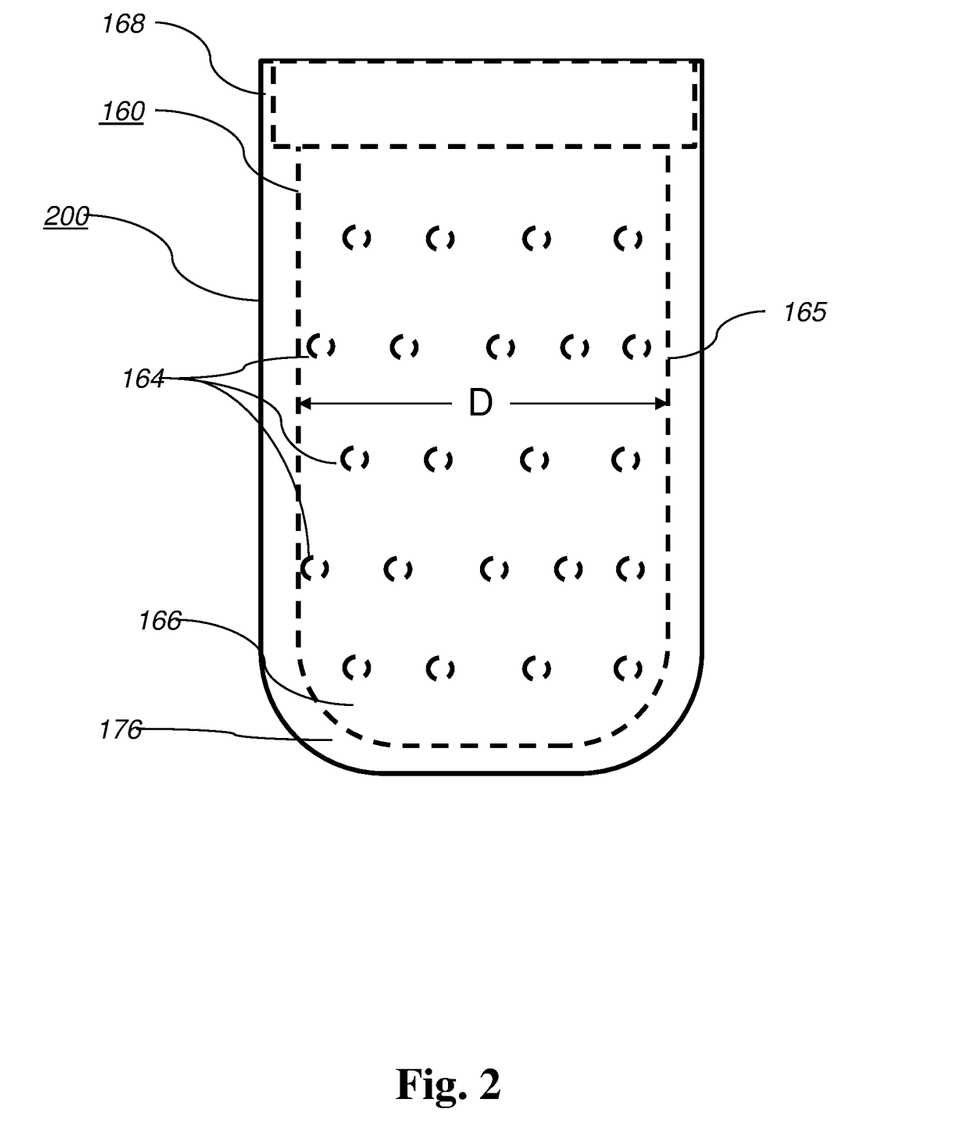
FIG. 2 is a schematic illustration of one step in a method of this disclosure to manufacture an example catheter tip.

Turning to FIG. 2, a schematic illustration of one step in an example method of this disclosure to manufacture an example catheter tip is shown, such as the manufacture of some or all of assembly 40. In some examples, the solution of this disclosure uses electroplating to metallize components, including plastics such as polycarbonate and ABS. The system and methods of this disclosure use a removable insert and/or mold that can be electroplated to create a catheter tip including a dome. Once electroplated, the insert can be removed (e.g., by melting the insert, by dissolving the insert in acid, etc.) to leave behind the electroplated shell which now has formed the catheter tip. The electroplated catheter tip can then be electropolished to remove surface roughness and/or burrs. The solution of this disclosure includes using and/or manufacturing a plurality of inserts that can be processed simultaneously (e.g., see 100s-1000s of inserts being plated at the same time).

In particular, FIG. 2 depicts an example mold 200 from which insert 100 can be created. For example, insert 100 can be formed by molding a plastic material from mold 200, which as shown can be a size and shape of assembly 40. Mold 200 can be substantially cylindrical with a mid-section 165 to correspond to an outer surface of mid-section 155 of insert 100. Mold 200 can also include a dome region 176 to correspond to dome 166 of insert 100, as well as a base section 168 to correspond to base 158 of insert 100, and a plurality of irrigation hole regions 164 for corresponding holes 64 of assembly 40.

In order to position hole regions 164 in some examples, an irrigation hole diameter can be selected as well as a desired catheter tip wall thickness. A lateral and a vertical growth rate of the material can also be determined along with determining a size of an insert irrigation hole negative based on the irrigation hole diameter, the wall thickness, and the lateral and the vertical growth rate of the material. For example, a size of hole regions 164 can be set to approximately 0.0065" to offset lateral growth of electroplated material of approximately 0.0035" thickness.

In determining a size of an insert irrigation hole negative, the irrigation hole diameter of hole regions 164 can be added with the catheter tip wall thickness. Moreover, lateral and the vertical growth rate of the material can be predetermined at a ratio of approximately 1:1, though other ratios larger and smaller are contemplated as needed or required. Hole regions 164 can also be positioned, size, or otherwise created simultaneously. Hole regions 164 can be positioned by forming an irrigation hole pattern on one or more regions of insert 100 (e.g., dome cover 166) out of a secondary non-plateable material.

Hole regions 164 can also be created by being predetermined holes of insert 100. In certain examples, the hole diameter of one or multiple hole regions 164 in the irrigation hole pattern can be offset by a wall thickness of insert 100. Hole regions 164 in this example can be positioned by oversizing an operational catheter tip diameter by a wall thickness of finished assembly 40. Hole regions 164 can also be positioned by sizing a manufacture diameter of holes 64 by an operational catheter tip diameter plus a wall thickness of finished assembly 40.

Hole regions 164 of any hole pattern according to this disclosure can also be configured to be filled by the secondary non-plateable material. It is understood that hole regions 164 and/or holes 64 themselves associated with assembly 40 can also be created after the insert 100 has been electroplated and removed (e.g., by being drilled). The secondary non-plateable material in some examples can be overmolded onto insert 100.

Once molded, insert 100 can be correspondingly shaped as a generally tubular feature with an inner lumen and can include at least one plastic, such as Acrylonitrile Butadiene Styrene (ABS) and Polycarbonate. The depicted shape of insert 100 is merely exemplary and other shapes and designs are contemplated as needed or required. Insert 100 can be formed in mold 200 from a variety of techniques, including injection molding, open molding, resin transfer molding (e.g., a castable resin), high-volume molding, compression molding, additive manufacturing, and the like. Insert 100 can be a negative to a domelike shape with dome section 166. The outer diameter D of insert 100 can be set or otherwise be based on a desired diameter of finished assembly 40. For example, diameter D can be 0.091" to simulate the inner diameter of assembly 40.

Figure 3:
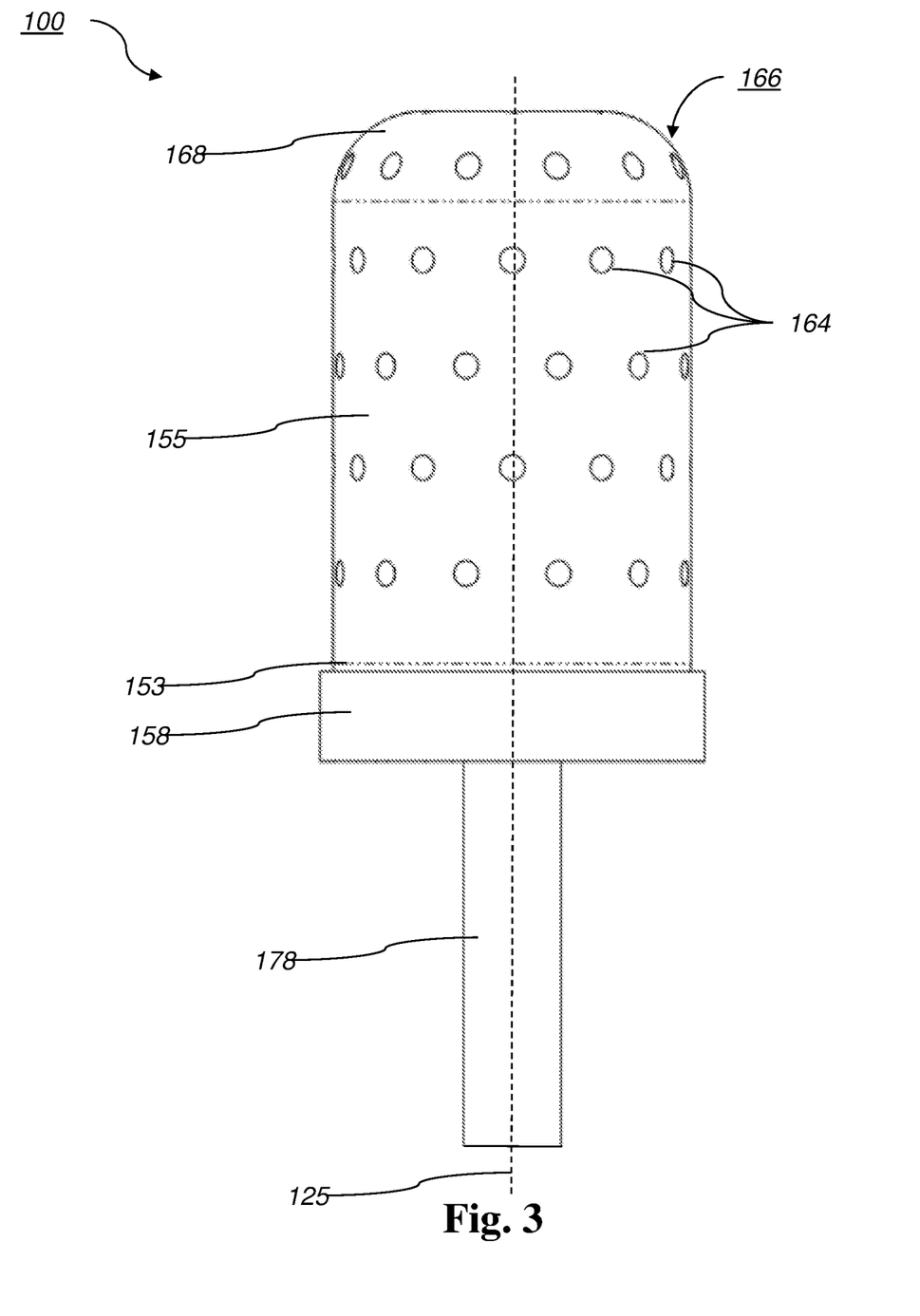
FIG. 3 is a schematic illustration of one step in a method of this disclosure to manufacture an example catheter tip.

Once one or more inserts 100 are formed, as shown in FIG. 3, a conductive material can be electroplated along an inner surface of insert 100 thereby creating an electroplated shell used with assembly 40, along with any corresponding selectively positioned holes 64. In some examples, a plurality of shells for a corresponding plurality of assemblies 40 and holes 64 can be created simultaneously. Insert 100 in FIG. 3 includes dome cover 166 with the dome-support 168, each corresponding to similar features of assembly 40 once electroplated. Insert 100 also includes one or more hole regions 164 which have been selectively positioned between inner and outer surfaces of insert 100 by mold 200, including on or about dome cover 166 and mid-section 155. While not shown, hole regions 164 can also be positioned on or about base 158, which can be located at the proximal end of insert 100. It is understood that insert 100 can include an internal lumen for directing irrigation ultimately into the inside of cavity of assembly 40.

In some examples, methods of electroplating the conductive material with the inner surface of insert 100 can include vapor deposition or some other chemical deposition process that deposits a thin layer of the conductive material over the inner surface of insert 100. The conductive material can completely cover, or plate, the inner walls of insert 100 and one or more computing systems can control the entire process of electroplating and/or insert 100 removal. In some examples, the conductive material can also be electroplated over insert 100 by axially aligning a pin 78 with a longitudinal axis 125 of insert 100 and holding, by the pin 78, the insert 100 during the electroplating.

In some examples, a lower edge on or adjacent base 158 of insert 100 can be thickened, as shown. The lower edge can be thickened with the secondary non-plateable material to prevent formation of a rounded edge thereabout. A step 153 can be used to thicken the lower edge, whereby the step 153 can have a height of approximately 0.002" or any other height needed ore required.

After insert 100 has been electroplated with the conductive material, insert 100 can be removed thereby leaving the catheter tip of assembly 40, and corresponding dome 66 and holes 64. Insert 100 can be removed from the conductive, electroplated material by applying heat (e.g., melting) to the insert 100 thereby leaving behind dome cover 66, midsection 55, base 58 and other corresponding regions of assembly 40. Insert 100 is also contemplated for removal by dissolving insert 100 in acid thereby leaving behind assembly 40. Once insert 100 is removed, assembly 40 can be electropolished. In some examples, electropolishing assembly 40 can include removing surface roughness and/or burrs from the electroplated material formed previously with insert 100. In some examples, assembly 40, and any constituent parts thereto manufactured with one or more of the herein disclosed steps can be finished to include a fingerprint, such as a unique marking, identifier or the like. Such markings and/or identifiers can include but not be limited to surface roughness, unique edges to the part certain sharpness, and the like.

Figure 4:
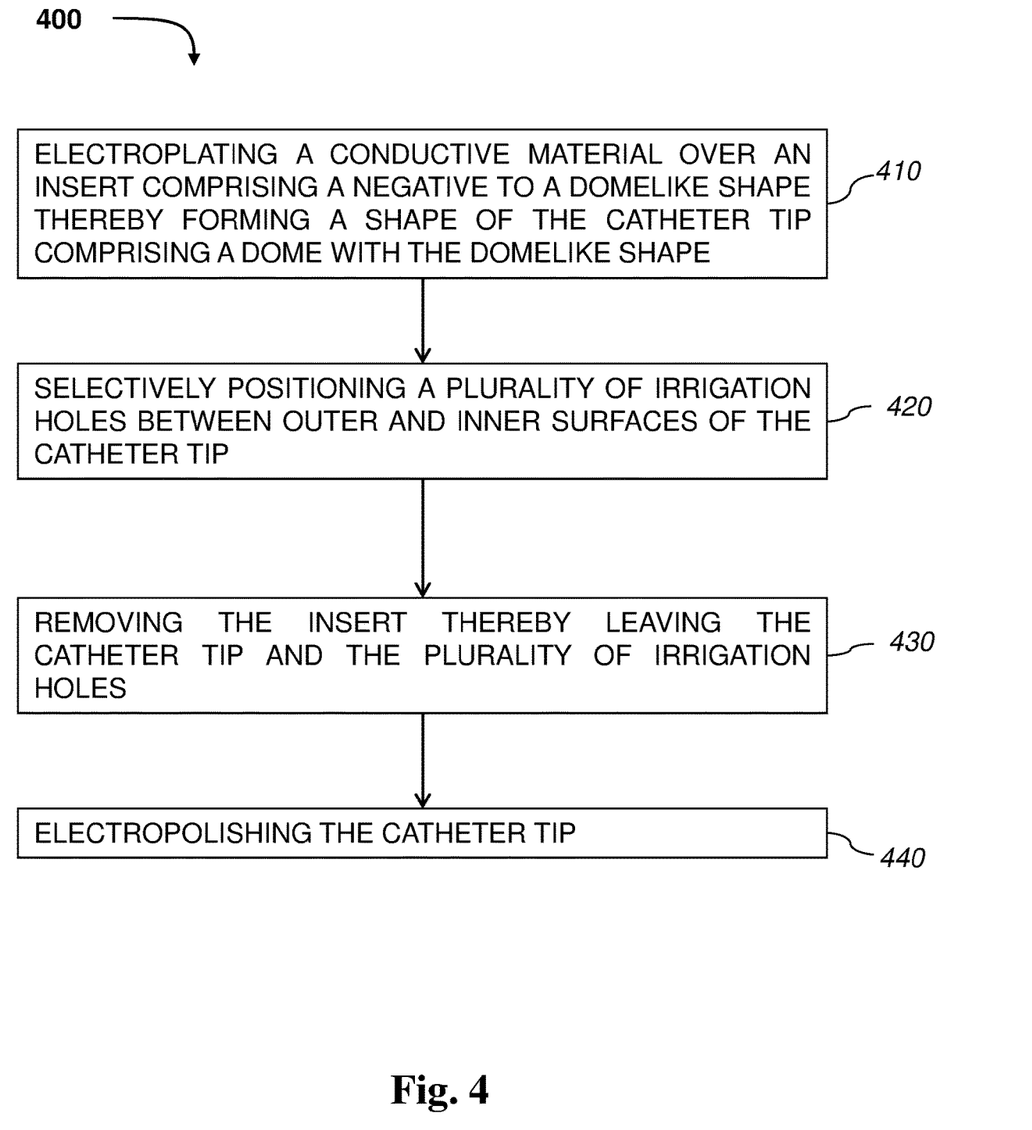
FIG. 4 is an illustration of a flow diagram illustrating an example method according to aspects of the present disclosure.

FIG. 4 is a flow diagram illustrating an example method 400 of manufacturing a catheter tip according to one example of this disclosure. Step 410 of method 400 can include electroplating a conductive material over an insert comprising a negative to a domelike shape thereby forming a shape of the catheter tip comprising a dome with the domelike shape. Step 420 of method 400 can include selectively positioning a plurality of irrigation holes between outer and inner surfaces of the catheter tip. Step 430 of method 400 can include removing the insert thereby leaving the catheter tip and the plurality of irrigation holes. Step 440 of method 400 can include electropolishing the catheter tip.

The method 400 can include additional steps as would be appreciated and understood by a person of ordinary skill in the art. For example, method 400 can include forming the insert by molding a plastic material from a mold of a size and shape of the catheter tip. The example method 400 can be performed by an example system, as disclosed herein, a variation thereof, or an alternative thereto as would be appreciated and understood by a person of ordinary skill in the art.

Figure 5:
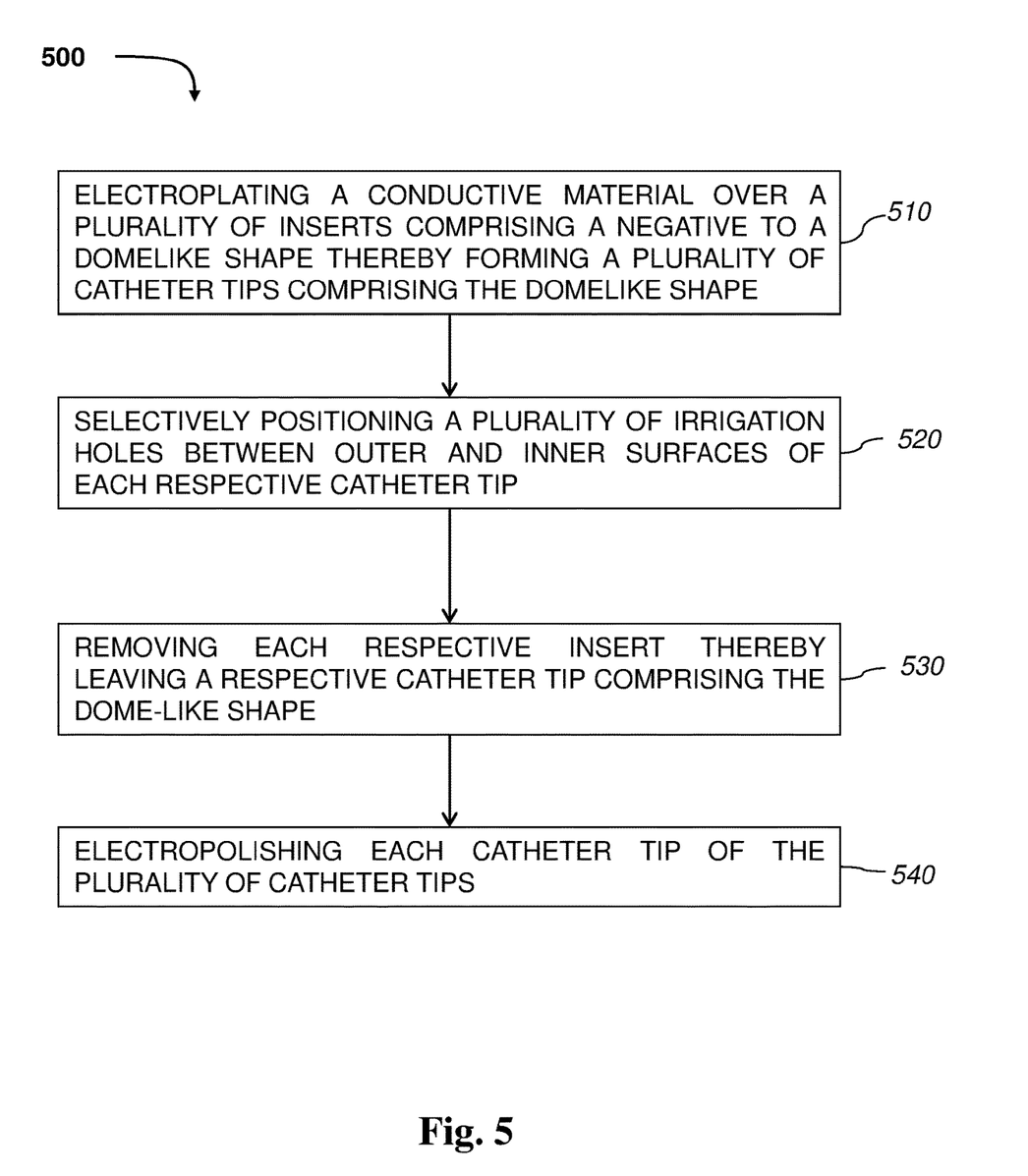
FIG. 5 is an illustration of a flow diagram illustrating an example method according to aspects of the present disclosure.

FIG. 5 is a flow diagram illustrating an example method 500 of manufacturing a plurality of catheter tips according to one example of this disclosure. Step 510 of method 500 can include electroplating a conductive material over a plurality of inserts comprising a negative to a domelike shape thereby forming a plurality of catheter tips comprising the domelike shape. Step 520 of method 500 can include selectively positioning a plurality of irrigation holes between outer and inner surfaces of each respective catheter tip. Step 530 of method 500 can include removing each respective insert thereby leaving a respective catheter tip comprising the dome-like shape. Step 540 of method 500 can include electropolishing each catheter tip of the plurality of catheter tips.

The method 500 can include additional steps as would be appreciated and understood by a person of ordinary skill in the art. For example, method 500 can include forming each respective insert by molding a plastic material from a mold of a size and shape of each respective catheter tip. The example method 500 can be performed by an example system, as disclosed herein, a variation thereof, or an alternative thereto as would be appreciated and understood by a person of ordinary skill in the art.

Figure 6:
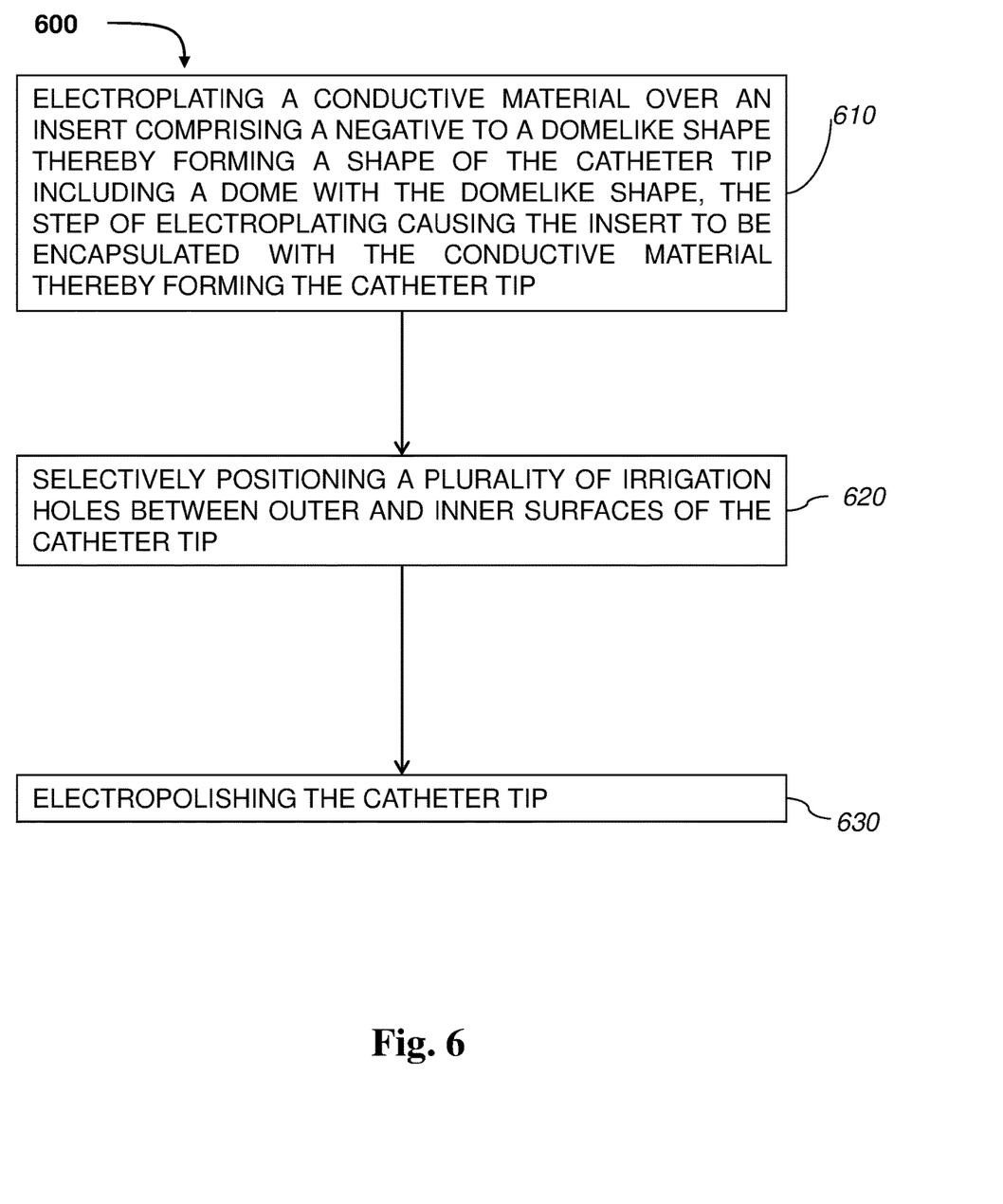
FIG. 6 is an illustration of a flow diagram illustrating an example method according to aspects of the present disclosure.

FIG. 6 is a flow diagram illustrating an example method 600 of manufacturing a catheter tip according to one example of this disclosure. Step 610 of method 600 can include electroplating a conductive material over an insert being a negative to a domelike shape and thereby forming a shape of the catheter tip to be a dome with the domelike shape. The step of electroplating causes the insert to be encapsulated with the conductive material thereby forming the catheter tip. Step 620 of method 600 can include selectively positioning a plurality of irrigation holes between outer and inner surfaces of the catheter tip. Step 630 of method 600 can include electropolishing the catheter tip.

Figure 7:
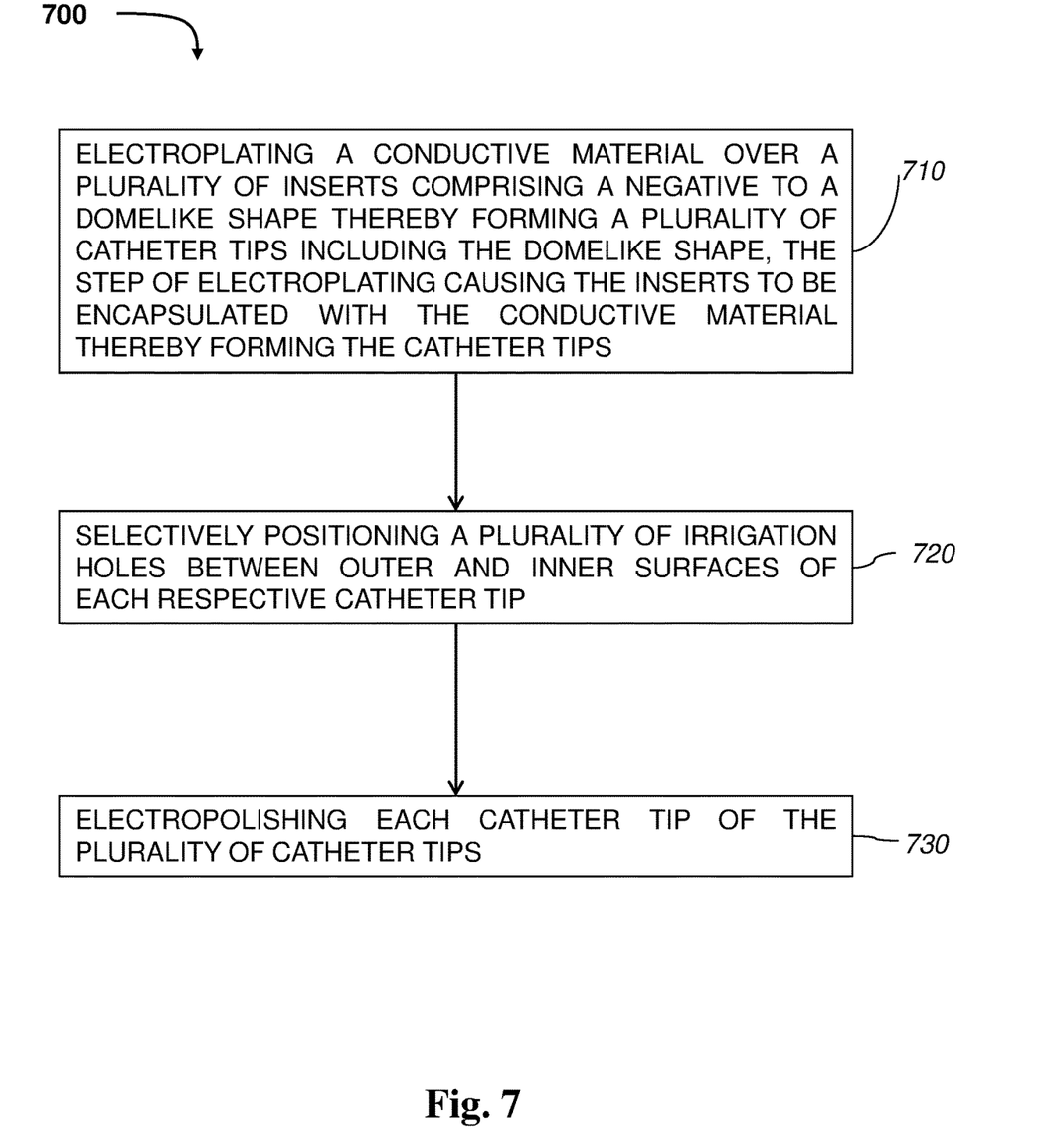
FIG. 7 is an illustration of a flow diagram illustrating an example method according to aspects of the present disclosure.

FIG. 7 is a flow diagram illustrating an example method 700 of manufacturing a plurality of catheter tips according to one example of this disclosure. Step 710 of method 700 can include electroplating a conductive material over a plurality of inserts comprising a negative to a domelike shape thereby forming a plurality of catheter tips having the domelike shape. The step of electroplating causing the inserts to be encapsulated with the conductive material thereby forming the catheter tips. Step 720 of method 700 can include selectively positioning a plurality of irrigation holes between outer and inner surfaces of the catheter tip. Step 730 of method 700 can include electropolishing the catheter tip.

Figure 8:
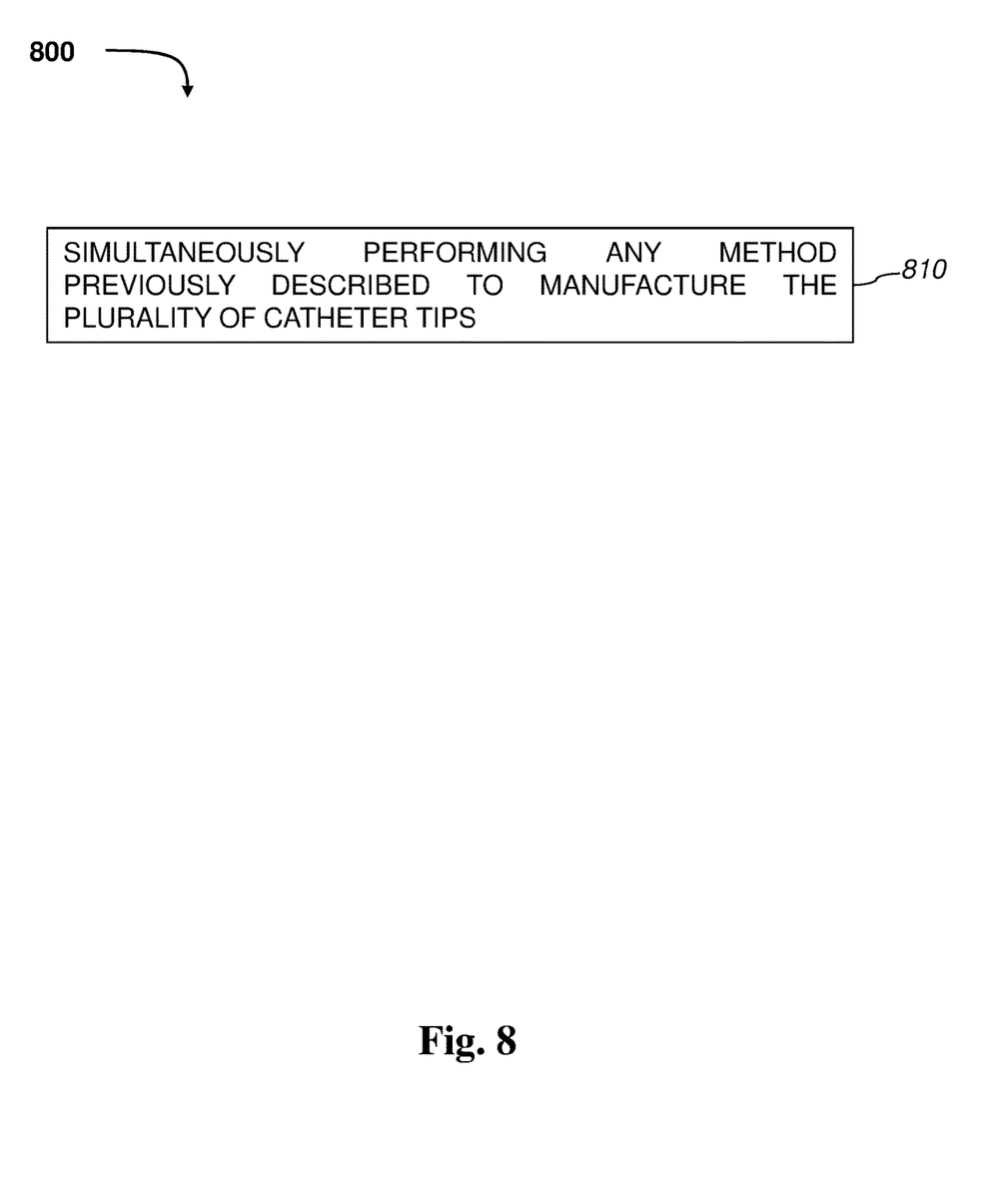
FIG. 8 is an illustration of a flow diagram illustrating an example method according to aspects of the present disclosure.

FIG. 8 is a flow diagram illustrating an example method 800 of manufacturing a plurality of catheter tips according to one example of this disclosure. Step 810 of method 800 can include simultaneously performing any method previously described to manufacture the plurality of catheter tips.

In some examples, the insert can be formed by applying a negative photoresistive formed mask coating to the negative molded part at the location of each irrigation hole that is sized to irrigation hole target and wall thicknesses to account for lateral growth. In some examples, a 0.003" hole in a 0.005" thick dome can include a photoresist dot of 0.013". A masked area of this example could prohibit surface plating on the masked area and permit annular growth from the surrounding palatable surface. By controlling the thickness of the plate and/or maintaining approximately 1:1 plate height:width ratio, the resulting hole size can meet the target. In this respect, a negative photoresist process can work by coating the negative molded part in a layer of photocrosslinking (e.g., SU-8 epoxy-based polymer) or photopolymeric (e.g., methyl methacrylate) material then exposing the hole pattern locations to an appropriate curing treatment (e.g., e-beam or UV light). In some examples, a photoresist developing agent can then be applied to remove the none-developed layers leaving only the resist layer in the pattern and sizing desired. In some examples, the electrode material may not grow from this surface so the irrigation hole can remain open. This example is particularly advantageous as it can leave an inset shape (e.g., a circle) on the inside of the created electrode of the diameter and thickness of the photoresist deposit used to create the irrigation hole, which can be created as the electrode metal grows over the edge of the photoresist coating.

The descriptions contained herein are examples of embodiments of the disclosure and are not intended in any way to limit the scope of the disclosure. As described herein, the disclosure contemplates many variations and modifications, including any of the herein discussed methods, steps, catheter tips, and solutions to manufacture a plurality of catheter tips simultaneously. These modifications would be apparent to those having ordinary skill in the art to which this disclosure relates and are intended to be within the scope of the claims which follow.

What is claimed is:

1. A method of manufacturing a catheter tip, comprising the steps of:
    forming an insert comprising a negative to a domelike shape;
    overmolding a secondary non-plateable material onto the insert at selected locations;
    electroplating a conductive material over the insert thereby forming a shape of the catheter tip comprising a dome with the domelike shape, the electroplating forming a plurality of irrigation holes between outer and inner surfaces of the catheter tip at the selected locations;

removing the insert thereby leaving the catheter tip and the plurality of irrigation holes; and electropolishing the catheter tip.

2. The method of claim 1, the catheter tip being generally tubular with a domelike cover.

3. The method of claim 1, the insert being generally tubular with an inner lumen.

4. The method of claim 1, the insert comprises a plastic comprising Acrylonitrile Butadiene Styrene (ABS).

5. The method of claim 1, the insert comprises a plastic comprising Polycarbonate.

6. The method of claim 1, the conductive material comprises at least one of gold, palladium, and platinum.

7. The method of claim 1, the step of selectively positioning the plurality of irrigation holes comprises the steps of:
selecting an irrigation hole diameter;
selecting a catheter tip wall thickness;
determining a lateral and a vertical growth rate of the material; and
determining a size of an insert irrigation hole negative based on the irrigation hole diameter, the wall thickness, and the lateral and the vertical growth rate of the material.

8. The method of claim 7, the lateral and the vertical growth rate of the material is 1:1; and the step of determining a size of an insert irrigation hole negative comprises adding the irrigation hole diameter with the catheter tip wall thickness.

9. The method of claim 1, the step of selectively positioning the plurality of irrigation holes is done simultaneously.

10. The method of claim 1, the step of electroplating the conductive material over the insert comprises:
axially aligning a pin with a longitudinal axis of the insert; and
holding, by the pin, the insert during electroplating.

11. The method of claim 1, further comprising:
setting an outer diameter of the insert to an inner diameter of the catheter tip.

12. The method of claim 1, further comprising:
positioning a step of the secondary non-plateable material at a lower edge adjacent a base of the catheter tip, the step comprising a height of approximately 0.002" thereby thickening the lower edge and preventing formation of a rounded edge.

13. The method of claim 1, further comprising:
offsetting a hole diameter of one or more holes in a hole pattern by a wall thickness.

14. The method of claim 13, further comprising:
maintaining, following the step of selectively positioning the plurality of irrigation holes and the step of removing the insert, a 1:1 ratio of lateral and vertical growth of the conductive material.

15. A method of manufacturing a plurality of catheter tips, the method comprising:
forming a plurality of inserts comprising a negative to a domelike shape;
overmolding a secondary non-plateable material onto each insert of the plurality of inserts at selected locations;
electroplating a conductive material over the plurality of inserts thereby forming the plurality of catheter tips comprising the domelike shape, the electroplating forming a plurality of irrigation holes between outer and inner surfaces of each respective catheter tip at the selected locations;
removing each respective insert thereby leaving a respective catheter tip comprising the domelike shape; and
electropolishing the catheter tips of the plurality of catheter tips.

16. The method of claim 15, the step of selectively positioning the plurality of irrigation holes comprises the steps of:
selecting an irrigation hole diameter;
selecting a catheter tip wall thickness;
determining a lateral and a vertical growth rate of the material; and
determining a size of an insert irrigation hole negative based on the irrigation hole diameter, the wall thickness, and the lateral and the vertical growth rate of the material.

17. The method of claim 16, the lateral and the vertical growth rate of the material is 1:1; and the step of determining a size of an insert irrigation hole negative comprises adding the irrigation hole diameter with the catheter tip wall thickness.

18. A method of manufacturing a plurality of catheter tips, the method comprising:
forming a plurality of inserts comprising a negative to a domelike shape;
overmolding a secondary non-plateable material onto each insert of the plurality of inserts at selected locations;
electroplating a conductive material over the plurality of inserts thereby forming the plurality of catheter tips comprising the domelike shape, the step of electroplating causing the inserts to be encapsulated with the conductive material thereby forming the catheter tips and forming a plurality of irrigation holes between outer and inner surfaces of each respective catheter tip at the selected locations; and
electropolishing the catheter tips of the plurality of catheter tips.

19. The method of claim 18 wherein the secondary non-plateable material comprises Nylon.

20. The method of claim 18 wherein the secondary non-plateable material comprises polypropylene.

\* \* \* \* \*